United States Patent
Budman

(10) Patent No.: US 6,338,818 B2
(45) Date of Patent: Jan. 15, 2002

(54) AROMA SENSORY STIMULATION IN MULTIMEDIA

(75) Inventor: Mark Budman, Vestal, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 09/758,901

(22) Filed: Jan. 11, 2001

Related U.S. Application Data

(62) Division of application No. 09/421,908, filed on Oct. 20, 1999, now Pat. No. 6,241,944, which is a division of application No. 09/094,280, filed on Jun. 9, 1998, now Pat. No. 6,024,783.

(51) Int. Cl.[7] .................................................. A61L 9/00
(52) U.S. Cl. ............................. 422/4; 96/222; 261/26; 261/107; 261/DIG. 65; 422/5; 422/108; 422/110; 422/122; 422/123; 422/124
(58) Field of Search ............... 261/26, 107, DIG. 16, 261/65; 96/222; 422/4, 5, 122, 123, 124, 125, 108, 110

(56) References Cited

U.S. PATENT DOCUMENTS

| | | |
|---|---|---|
| 3,585,991 A | 6/1971 | Balamuth |
| 4,556,539 A | 12/1985 | Spector |
| 4,603,030 A | 7/1986 | McCarthy |
| 4,629,604 A | 12/1986 | Spector |
| 4,647,433 A | 3/1987 | Spector |
| 4,695,434 A | 9/1987 | Spector |
| 4,771,344 A | 9/1988 | Fallacaro et al. |
| 4,859,103 A | 8/1989 | Wittek ........................ 401/108 |
| 5,071,621 A | 12/1991 | Tokuhiro et al. |
| 5,105,133 A | 4/1992 | Yang |
| 5,171,485 A | 12/1992 | Ryan |
| 5,192,342 A | 3/1993 | Baron et al. |
| 5,207,523 A | 5/1993 | Wittek ........................ 401/107 |
| 5,297,988 A | 3/1994 | Nishino et al. |
| 5,318,503 A | 6/1994 | Lord |
| 5,398,070 A | 3/1995 | Lee |
| 5,565,148 A | 10/1996 | Pendergrass, Jr. |
| 5,577,668 A | 11/1996 | King et al. |
| 5,591,409 A | 1/1997 | Watkins |
| 5,724,256 A | 3/1998 | Lee et al. |
| 5,725,323 A | 3/1998 | Wittek ........................ 401/114 |
| 5,760,873 A | 6/1998 | Wittek |
| 5,832,320 A | 11/1998 | Wittek ........................ 396/106 |
| 5,958,346 A | 9/1999 | Evans, Jr. |
| 5,963,302 A | 10/1999 | Wittek ......................... 352/38 |
| 5,972,290 A | 10/1999 | De Sousa |
| 6,024,783 A | 2/2000 | Budman |
| 6,025,902 A | 2/2000 | Wittek ......................... 352/85 |

FOREIGN PATENT DOCUMENTS

| | | |
|---|---|---|
| EP | 0 611 476 B1 | 1/1997 |
| EP | 0 775 003 B1 | 4/1999 |
| EP | 0 732 132 B1 | 8/2000 |

OTHER PUBLICATIONS

Gerber et al., "Scent Generator", IBM Technical Disclosure Bulletin, vol. 38, No. 11, pp. 429–430, Nov. 1995.

Primary Examiner—Krisanne Thornton
(74) Attorney, Agent, or Firm—Arthur J. Samodovitz

(57) ABSTRACT

An apparatus for the remote or local delivery of stored or real-time aroma sensory information to an end user of a multimedia device. The present invention includes an aroma converter for encoding aroma information into electrical signals, a delivery system for delivering the electrical signals, and a retrieval system for receiving and processing the electrical signals to control the aroma or combination of aromas emitted by one or more aroma release chambers.

12 Claims, 2 Drawing Sheets

AROMA SENSORY STIMULATION IN MULTIMEDIA

This application is a division of 09/421,908 filed Oct. 20, 1999 now U.S. Pat. No. 6,241,944 which is a division of U.S. Ser. No. 09/094,280 filed Jun. 9, 1998 now U.S. Pat. No. 6,024,783.

FIELD OF THE INVENTION

The present invention is in the field of multimedia devices. More particularly, the present invention provides an apparatus for the delivery of aroma sensory information to a user of a multimedia device.

BACKGROUND OF THE INVENTION

Currently available multimedia devices, such as computers, video games, and televisions, are designed to provide visual and audio sensory information to a user. In many applications, however, it may be desirable to additionally provide aroma sensory information to enhance the realism and appeal of the information presented to a user by the multimedia device.

SUMMARY OF THE INVENTION

The present invention provides an apparatus for the remote or local delivery of stored or real-time aroma sensory information to an end user of a multimedia device. The present invention includes an aroma converter for encoding aroma information into electrical signals. The electrical signals may be delivered to an end user in analog or digital form using a wide variety of delivery systems, including, but not limited to, magnetic media (e.g., a floppy or hard disk), optical or magneto-optical media (e.g., a compact disc (CD)), radio, television, or satellite transmitters, or telephone or cable systems. The electrical signals are retrieved and processed to control the aroma or combination of aromas emitted by one or more aroma release chambers. Many types of retrieval systems may be used to receive and process the electrical signals. The retrieval system may include, for example, a personal computer or computer peripheral, a video game system, a television set, home entertainment/theater system, or a dedicated, stand-alone module.

Generally, the present invention provides an apparatus for aroma sensory stimulation comprising:
  an aroma converter for encoding aroma information into electrical signals;
  a control device for processing the electrical signals; and
  at least one aroma release chamber, each aroma release chamber configured to selectively generate a predetermined aroma under control of the control device, each aroma release chamber comprising:
  a container having an opening;
  a door for selectively covering the opening in the container;
  an aroma element, located within the container, for emitting a predetermined aroma when heated;
  a heating system for selectively heating the aroma element;
  an air filtration system for filtering air entering the container; and
  an air displacement system for selectively displacing a stream of air through the container to release the predetermined aroma.

BRIEF DESCRIPTION OF THE DRAWINGS

The features of the present invention will best be understood from a detailed description of the invention and a preferred embodiment thereof selected for the purposes of illustration and shown in the accompanying drawings in which.

DETAILED DESCRIPTION OF THE INVENTION

Figure 1:
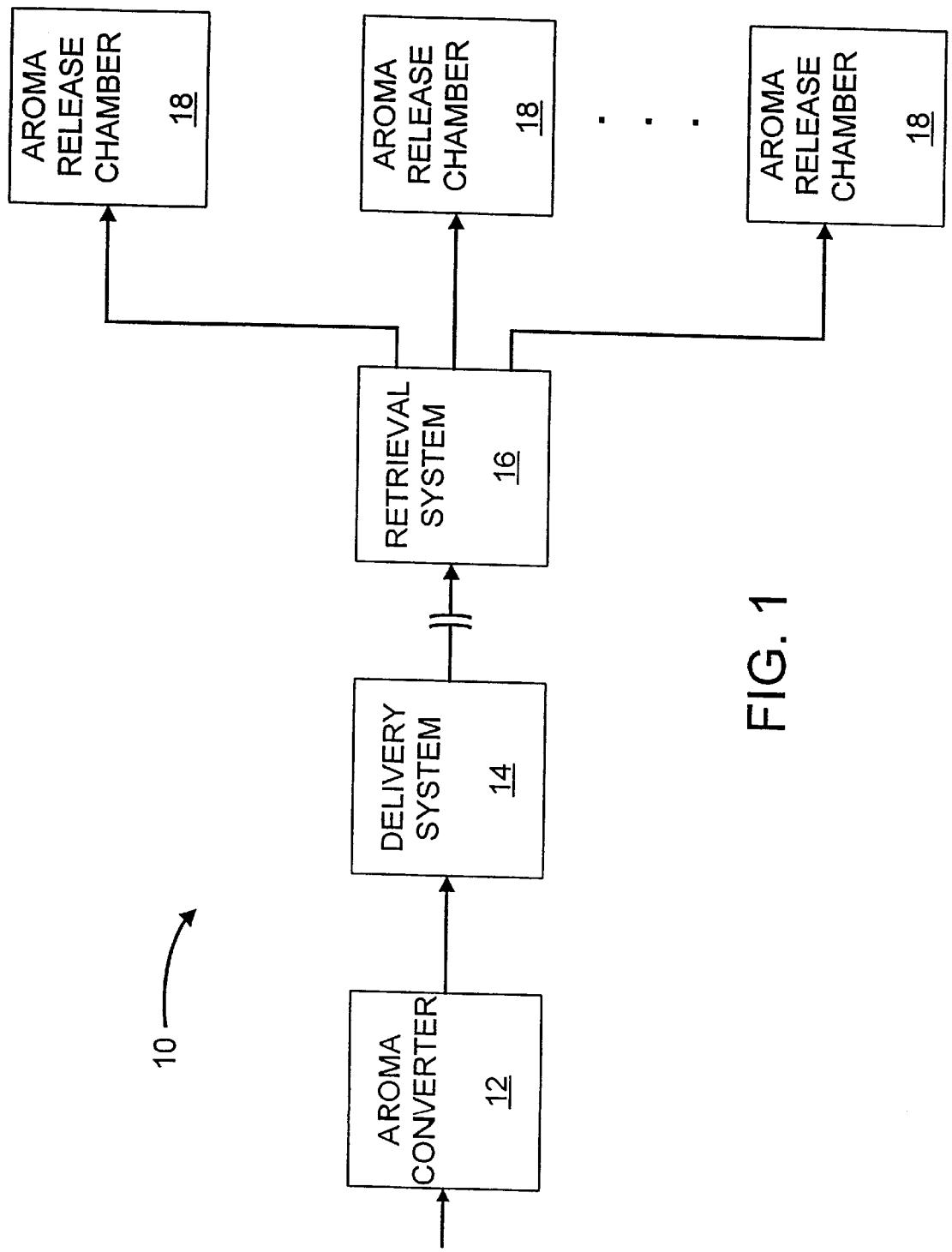
FIG. 1 illustrates a block diagram of an aroma sensory stimulation apparatus according to the present invention.

The features and advantages of the present invention are illustrated in detail in the accompanying drawings, wherein like reference numerals refer to like elements throughout the drawings.

A block diagram of an aroma sensory stimulation apparatus, generally designated as 10, according to the present invention, is illustrated in FIG. 1.

The aroma sensory stimulation apparatus 10 includes an aroma converter 12 for encoding aroma information into electrical signals. The aroma information may be converted into analog or digital electrical signals, depending on such factors as the type of delivery and retrieval systems to be used in a given implementation of the aroma sensory stimulation apparatus 10.

The aroma information may be encoded using a wide variety of techniques. For example, an aroma sensory stimulation apparatus 10 configured to produce sixteen (16) distinct aromas may encode the aroma information using a 4-bit digital word or sixteen distinct voltage levels. The scent of a rose, for example, may be encoded as "0001," while the aroma of a rotten egg may be encoded as "1111." An error correcting technique may be employed to ensure the correct delivery of the encoded aroma information.

The electrical signals produced by the aroma converter 12 are delivered to a local or remote end user in an analog or digital format by a delivery system 14. The delivery system 14 may take on a wide variety of forms. For example, the delivery system 14 may comprise a data carrier such as a floppy or hard disk, a compact disc, or other type of magnetic, optical or magneto-optical media, having the electrical signals saved or encoded thereon. Alternately, the delivery system may comprise a system for transmitting the electrical signals via radio, television, satellite, telephone, or the Internet.

A retrieval system 16 is provided to retrieve and process the electrical signals delivered by the delivery system 14 to control the aroma or combination of aromas emitted by one or more aroma release chambers 18. The retrieval system 16 may also take on a wide variety of forms, depending on the type of delivery system 14 being used, the format of the electrical signals provided by the delivery system 14, as well as other factors. For example, the retrieval system 16 may comprise a personal computer, a video game system, or a television set. It should be clear, however, that many other types of delivery and retrieval systems 14, 16 may be used without departing from the intended scope of the present invention as set forth in the accompanying claims.

Figure 2:
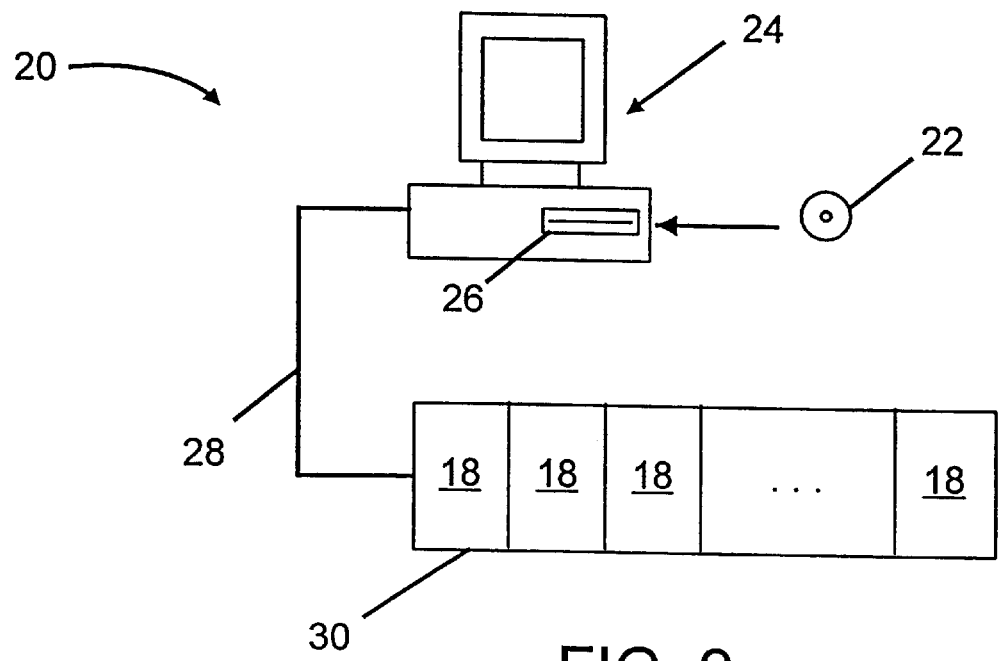
FIG. 2 illustrates an aroma sensory stimulation apparatus according to a preferred embodiment of the present invention.

An aroma sensory stimulation apparatus 20 according to a preferred embodiment of the present invention is illustrated in FIG. 2. In this embodiment, the delivery system comprises a compact disc 22 having aroma information encoded thereon. A computer system 24 including a compact disc reader 26 serves as the retrieval system for accessing and processing the aroma information stored on the compact disc 22. The computer system 24 transmits control signals via a cable 28 to an aroma-release system 30 containing at least one of the aroma release chambers 18. Based on the aroma information, at least one of the aroma release chambers 18 is actuated in response to the control signals transmitted by the computer system 24 to generate a predetermined aroma or combination or aromas.

Figure 3:
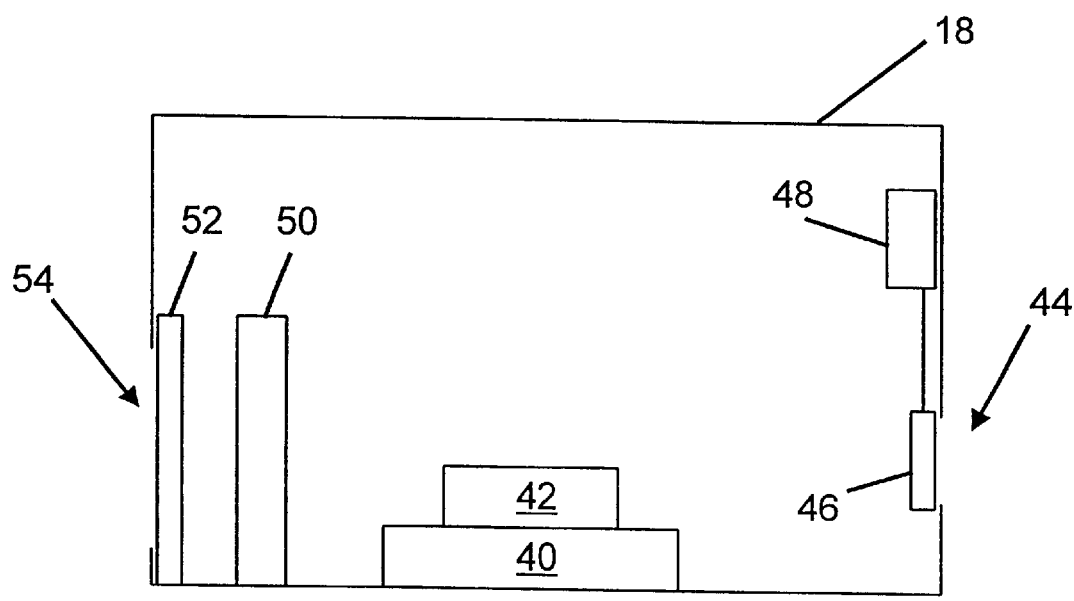
FIG. 3 is a side cross-sectional view of an aroma release chamber in accordance with a preferred embodiment of the present invention.

A side cross-sectional view of an aroma release chamber 18 in accordance with a preferred embodiment of the present invention is illustrated in FIG. 3. The aroma release chamber 18 includes a selectively controlled hot plate 40 which operates in response to control signals provided by the computer system 24 over the cable 28. A replaceable aroma stick 42 that emits a particular aroma when heated, or other type of solid, liquid, or gaseous heat actuated aroma source, is located within the aroma release chamber 18. Preferably, the aroma stick 42 is positioned directly on the hot plate 40.

The aroma release chamber 18 further includes an opening 44 covered by a door 46. An electromagnet 48 operates in response to control signals provided by the computer system 24 via the cable 28 to selectively open or close the door 46. Preferably, the door 46 is biased toward a closed position by a spring or other biasing means (not shown). A fan 50 is provided to displace a stream of air through the aroma release chamber 18 and out of the opening 44 to release the aroma generated when the aroma stick 42 is heated by the hot plate 40.

An air filtration system 52 is located over an air intake opening 54 to filter the stream of air being drawn into the aroma release chamber 18 by the fan 50. The air filtration system 52 is provided to remove previously emitted aromas from the stream of air being drawn into the aroma release chamber 18 to allow precise control of the aroma subsequently emitted by the chamber 18.

In operation, the computer system 24 retrieves and processes at least a portion of the aroma information encoded on the compact disc 22. The computer system 24 then transmits control signals to one or more predetermined aroma release chambers 18 over the cable 28 to generate the aroma or combination of aromas defined by the aroma information. Upon receipt of the control signals, the hot plate 40, the electromagnet 48 that opens the door 46, and the fan 50 in each of the predetermined aroma release chambers 18 are activated, thereby releasing the desired aroma or combination of aromas. The predetermined aroma release chambers 18 may each be activated for an identical period of time, or for different lengths of time to release different strengths of their respective aromas. Each of the predetermined aroma release chambers 18 is deactivated in response to control signals transmitted by the computer system 24 to prevent any further aroma release. When deactivated, the hot plate 40, fan 50, and electromagnet 48 are turned off, and the door 46 seals the opening 44 in the aroma release chamber 18. This process is repeated, as necessary, according to the aroma information encoded on the compact disc 22.

The foregoing description of the present invention has been presented for purposes of illustration and description. It is not intended to be exhaustive or to limit the invention to the precise form disclosed, and many modifications and variations are possible in light of the above teaching. For example, several aroma sticks, each corresponding to a different aroma, may be located within the same aroma release chamber. In this manner, a combination of aromas may be produced using a single aroma release chamber. Further, the aroma stick and hot plate in each aroma release chamber may be replaced with a solid, liquid, or gaseous, non-heat actuated aroma source. For example, the aroma source may comprise an odorant cassette, such as that disclosed in U.S. Pat. No. 5,724,256, incorporated herein by reference. Such modifications and variations that may be apparent to a person skilled in the art are intended to be included within the scope of this invention as defined by the accompanying claims.

I claim:

1. A method for dispensing a composite aroma, said method comprising the steps of:

receiving a control signal indicative of said composite aroma;

opening a plurality of different chambers corresponding to said control signal, each chamber containing a different aroma source substance, one of said plurality of chambers being opened for a total duration different than another of said plurality of chambers to correspond to said control signal; and using forced air to draw and mix aromas from said plurality of different chambers while said chambers are open to yield said composite aroma, without removing said aroma source substances from their respective chambers.

2. A system for dispensing a composite aroma, said system comprising:

a multiplicity of chambers, each chamber containing a different aroma source substance;

a processor to receive and process an aroma signal indicative of said composite aroma and generate a corresponding control signal;

a control, responsive to said control signal, to open a plurality of said chambers corresponding to said control signal, one of said plurality of chambers being opened for a total duration different than another of said plurality of chambers to correspond to said control signal; and a fan to draw and mix aromas from said plurality of different chambers while said chambers are open to yield said composite aroma without removing said aroma source substances from their respective chambers.

3. A method as set forth in claim 1 wherein the duration that each of said chambers is open and the forced air draws the respective aroma determines in part the composite aroma.

4. A method as set forth in claim 1 wherein there are at least three different chambers which are opened in response to said control signal, each chamber containing a different aroma source substance, each of said three chambers being opened for a total duration different than the other two of said three chambers to correspond to said control signal.

5. A method as set forth in claim 4 wherein the duration that each of said chambers is open and the forced air draws the respective aroma determines in part the composite aroma.

6. A system as set forth in claim 2 wherein the duration that said control opens each of said chambers and the fan draws the respective aroma determines in part the composite aroma.

7. A system as set forth in claim 2 wherein said control opens at least three different chambers in response to said control signal, each chamber containing a different aroma source substance, said control opening each of said three chambers for a total duration different than the other two of said three chambers to correspond to said control signal.

8. A system as set forth in claim 7 wherein the duration that said control opens each of said chambers and the fan draws the respective aroma determines in part the composite aroma.

9. A method for dispensing a composite aroma, said method comprising the steps of:

receiving a control signal indicative of said composite aroma;

opening a plurality of different chambers corresponding to said control signal, each chamber containing a different aroma source substance, one of said plurality of chambers being opened for a total duration different than another of said plurality of chambers in accordance with said control signal; and using forced air to draw and mix aromas from said plurality of different chambers while said chambers are open to yield said composite aroma.

10. A method as set forth in claim 9 wherein the duration that each of said chambers is open and the forced air draws the respective aroma determines in part the composite aroma.

11. A system for dispensing a composite aroma, said system comprising:

a multiplicity of chambers, each chamber containing a different aroma source substance;

a processor to receive and process an aroma signal indicative of said composite aroma and generate a corresponding control signal;

a control, responsive to said control signal, to open a plurality of said chambers corresponding to said control signal, one of said plurality of chambers being opened for a total duration different than another of said plurality of chambers to correspond to said control signal; and a fan to draw and mix aromas from said plurality of different, open chambers to yield said composite aroma.

12. A system as set forth in claim 11 wherein the duration that said control opens each of said chambers and the fan draws the respective aroma determines in part the composite aroma.

* * * * *